United States Patent [19]

Udovich et al.

[11] Patent Number: 4,510,259

[45] Date of Patent: * Apr. 9, 1985

[54] CATALYSTS FOR THE PRODUCTION OF MALEIC ANHYDRIDE BY THE OXIDATION OF BUTANE

[75] Inventors: Carl A. Udovich, Joliet; Robert C. Edwards, Naperville, both of Ill.

[73] Assignee: Standard Oil Company (Indiana), Chicago, Ill.

[*] Notice: The portion of the term of this patent subsequent to Nov. 22, 2000 has been disclaimed.

[21] Appl. No.: 526,167

[22] Filed: Aug. 25, 1983

Related U.S. Application Data

[63] Continuation-in-part of Ser. No. 382,180, May 26, 1982, Pat. No. 4,416,802.

[51] Int. Cl.³ .......................... B01J 27/14; B01J 31/12
[52] U.S. Cl. .................................. 502/209; 502/210; 502/211; 502/170
[58] Field of Search ................ 502/209, 210, 211, 170

[56] References Cited

U.S. PATENT DOCUMENTS

| | | | |
|---|---|---|---|
| 3,832,359 | 8/1974 | Freerks et al. | 502/209 X |
| 3,888,886 | 6/1975 | Young et al. | 502/209 X |
| 3,985,775 | 10/1976 | Garrison | 502/209 |
| 4,002,650 | 6/1977 | Bever et al. | 549/260 |
| 4,016,105 | 4/1977 | Kerr | 502/209 |
| 4,147,661 | 4/1979 | Higgins et al. | 549/260 X |
| 4,151,116 | 4/1979 | McDermott | 502/209 X |
| 4,152,338 | 5/1979 | Kerr | 549/260 |
| 4,152,339 | 5/1979 | Kerr et al. | 549/260 |
| 4,178,464 | 12/1979 | Sokamoto et al. | 502/209 X |
| 4,283,288 | 8/1981 | Udovich et al. | 502/209 |

FOREIGN PATENT DOCUMENTS

| | | | |
|---|---|---|---|
| 2001256A | 7/1978 | United Kingdom . | |
| 2019839A | 11/1979 | United Kingdom | 502/209 |

*Primary Examiner*—William G. Wright
*Attorney, Agent, or Firm*—Gunar J. Blumberg; William T. McClain; William H. Magidson

[57] ABSTRACT

A process for the manufacture of a phosphorus-vanadium oxide and a phosphorus-vanadium-co-metal catalyst suitable for the oxidation of butane to maleic anhydride is disclosed. The catalyst is prepared by reacting, in an aqueous medium, a vanadium compound, inorganic acid and, if used, a metal oxide. Ortho-phosphoric acid is then added to form a soluble vanadium-phosphorus or a vanadium-phosphorus-metal catalyst. The acidified water is removed and aliphatic alcohols and either aromatic acids or aromatic anhydrides, or a mixture of these, are added and the alcohols are removed. The solid phosphorus-vanadium, or phosphorus-vanadium-metal oxide is recovered under vacuum.

35 Claims, No Drawings

CATALYSTS FOR THE PRODUCTION OF MALEIC ANHYDRIDE BY THE OXIDATION OF BUTANE

BACKGROUND OF THE INVENTION

This is a continuation-in-part application of Ser. No. 382,180 filed May 26, 1982 U.S. Pat. No. 4,416,802.

1. Field of the Invention

The field of this invention relates to processes for the manufacture of phosphorus, vanadium and phosphorus-vanadium-co-metal catalysts, suitable for the oxidation of butane to maleic anhydride.

2. Background

Maleic anhydride is of significant commercial interest throughout the world and is extensively used in the manufacture of alkyd resins. It is also a versatile intermediate of chemical synthesis. Consequently, large quantities of maleic anhydride are produced each year to satisfy these needs. The production of maleic anhydride by the catalytic oxidation of benzene and butene is well-known, and until recently, the principal method employed for the manufacture of maleic anhydride was by the air oxidation of benzene in the presence of certain heavy metal oxide catalysts. However, because of the inherent toxicity of benzene fumes, the trand has been to eliminate the utilization of benzene as a feedstock and newer facilities tend to utilize butane oxidation processes.

In general, catalysts proposed for the oxidation of butane to maleic anhydride have been based upon vanadium and phosphorus. In U.S. Pat. No. 3,293,268 it is disclosed that the oxidation of butane to maleic anhydride can be performed in the presence of a phosphorus-vanadium-oxygen-containing complex catalyst. Though this catalyst is capable of oxidizing butane, it does not give sufficiently high yields. Yields of maleic anhydride of only 30 to 50 weight percent are reported. Various activators, stabilizers and promoters have been disclosed in the prior art to improve the yields of maleic anhydride. References include U.S. Pat. Nos. 3,867,411; 3,832,359; 3,888,886; 4,002,650; 4,147,661; 4,149,992; 4,151,116; 4,152,338; 4,152,339; and British Application 2,019,839A. While the aforementioned prior art tends to bring about some improvement in the performance of the phosphorus-vanadium catalyst, there remains much room for improvement, particularly from the standpoint of high conversion, yield and catalyst life.

The object of the present invention is to provide a nonprecipitated method for the manufacture of phosphorus, vanadium and phosphorus-vanadium-co-metal oxide catalysts, by carrying out the reaction in both aqueous and non-aqueous solvents. A further object is to provide a process for the manufacture of maleic anhydride in the presence of the catalyst manufactured by the novel process.

Our catalyst is suitably prepared in aqueous solvents using inorganic acids. When using co-metals our catalyst is suitably prepared in aqueous solvents using inorganic acids. Otherwise the procedure is the same as described herein below. Suitable co-metals include molybdenum, zinc, uranium, tungsten, tin, bismuth, titanium, zirconium, niobium, chromium, and antimony which are introduced as their respective oxides. When the aqueous solution is clear, and substantial reduction of vanadium (V) to vanadium (IV) has taken place, phosphoric acid, such as 85 percent ortho-phosphoric acid, is added to form a soluble aqueous vanadium-phosphorus-metal oxide catalyst. A large quantity of water-hydrogen chloride is removed from the catalyst solution giving a thick syrup which is then diluted in a suitable alcohol having from about 1 to about 8 carbon atoms or other suitable organic solvent. An aromatic acid or an aromatic anhydride or a mixture of these is added to this alcoholic catalyst solution. Suitable alcohols are methanol, ethanol, 1-propanol, 2-propanol, 1-butanol, 2-butanol, 2-methyl-1-propanol, 2-methyl-2-propanol, and other alcohols containing from about 1 to about 8 carbon atoms. Suitable anhydrides are phthalic anhydride, trimellitic anhydride, pyromellitic dianhydride, benzoic anhydride, toluic anhydride, etc. Suitable aromatic acids are phthalic acid, trimellitic acid, benzoic acid, toluic acid, terephthalic acid, isophthalic acid, hemimellitic acid, trimesic acid, pyromellitic acid, 2,4-xylylic acid, isoxylylic acid, 2,6-xylylic acid, paraxylylic acid, mesitylenic acid, 2-ethylbenzoic acid, 3-ethylbenzoic acid, 4-ethylbenzoic acid, prehnitylic acid, durylic acid, mesitoic acid, pentamethyl benzoic acid, mellitic acid, etc.

In place of HCl, other acids capable of reducing vanadium can be utilized, such as HBr. Suitable metals include molybdenum, tungsten, zinc, uranium, chromium, tin, bismuth, zirconium, niobium, titanium, and antimony. Our catalyst has a much higher activity than catalysts of the prior art, such as those disclosed in U.S. Pat. No. 3,862,146, and U.S. Pat. No. 4,328,126. Our process recovers 100 percent of the vanadium feedstock, compared to the usual precipitative process which recovers only about 60 percent of the vanadium. Among the many advantages of our novel process for the manufacture of the catalyst can be cited the quantitative use of the expensive vanadium and the use of very cheap solvents, such as water and methanol or ethanol or aromatic acids or anhydrides and phosphoric acid.

The novel catalyst comprises a phosphorus-vanadium mixed oxide and a phosphorus-vanadium mixed oxide promoted by metals. The atomic ratio of the vanadium to phosphorus can suitably be in the range of 0.5:1 to 1.25:1.0. The total atomic ratio of co-metal to vanadium advantageously is in the range of 0.001:1 to 1:1. It is preferred that the total atomic ratio of molybdenum to vanadium should be in the range of 0.001:1 to 0.2:1. The atomic ratio of phosphorus to vanadium is suitably in the range of 0.8:1 to 2:1, preferably 1:1 to 1.5:1.

The co-metal, such as molybdenum, may be added as a compound together with vanadium, or separately introduced into the solution. Suitable molybdenum compounds comprise molybdenum oxide and most soluble molybdenum salts. If it is desired to improve physical properties of the catalysts, they may be treated with the suspension of an inert support; for example, alumina, titania, silicon carbide, kieselguhr, pumice, or silica. The catalyst may be reinforced with such materials at any stage in its preparation.

According to our process, the average valence of vanadium is in the range of about 3.8 to about 4.2. In our catalyst preparation, hydrous phosphoric acids or various anhydrous phosphoric acids may be used, including ortho-phosphoric, pyrophosphoric, triphosphoric acid or meta-phosphoric acid. Suitable vanadium compounds include: vanadium oxides, such as vanadium pentoxide, vanadium tetroxide and the like; vanadium oxyhalides, such as vanadyl chloride, vanadyl dichloride, vanadyl trichloride, vanadyl bromide, vanadyl dibromide, vanadyl tribromide, and the like; vanadium-containing acids, such as meta-vanadic acid, pyrovanadic acid, and the like; vanadium salts, such as ammonium meta-vanadate, vanadium sulfate, vanadium phosphate, vanadyl formate, vanadyl oxalate, and the like. However, vanadium pentoxide is preferred.

This invention also comprises a process for oxidizing butane to maleic anhydride by contacting it in the presence of oxygen with the novel catalyst. The oxidation of butane to maleic anhydride may be accomplished by contacting n-butane in low concentration in oxygen with the described catalyst. Air is entirely satisfactory as a source of oxygen, but synthetic mixtures of oxygen and diluent gases, such as nitrogen, may also be employed. Air enriched with oxygen may be used.

The gaseous feedstream to the oxidation reactors will normally contain air and about 0.2 to about 1.7 mole percent of n-butane. About 0.8 to about 1.5 mole percent of n-butane is satisfactory for optimum yield of maleic anhydride for the process of this invention. Although higher concentrations may be employed, explosive hazards may be encountered. Lower concentrations of butane, less than about one percent, of course, will reduce the total yield obtained at equivalent flow rates and, thus, are not normally economically employed. the flow rate of the gaseous stream through the reactor may be varied within rather wide limits, but the preferred range of operations is at the rate of about 100 to about 4000 cc of feed per cc of catalyst per hour, and more preferably about 1000 to about 2400 cc of feed per cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury at 25° C. A variety of reactors will be found to be useful, and multiple tube heat exchanger-type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at a relatively constant temperature and to have some medium to conduct heat from the reactors, such as lead and the like, but it has been found that eutectic salt baths are completely satisfactory. One such salt bath is a sodium nitrate, sodium nitrite, potassium nitrate, eutectic constant temperature mixture. An additional method of temperature control is to use a metal block reactor, whereby the metal surrounding the tube acts as a temperature regulating body. As will be recognized by those skilled in the art, the heat exchanger medium may be kept at the proper temperature by heat exchangers and the like. The reactor or reaction tubes may be iron, stainless steel, carbon steel, nickel, glass tubes, such as vycor, and the like. Both carbon steel and nickel tubes have excellent long life under the conditions of the reaction described herein. Normally, the reactors contain a preheat zone under an inert material, such as one-quarter inch Alundum pellets, inert ceramic balls, nickel balls, or chips, and the like, present at about one-half to about one-tenth the volume of the active catalyst present.

The temperature of reaction may be varied within some limits, but normally the reaction should be conducted at a temperature within a rather critical range. The oxidation reaction is exothermic, and once reaction is underway, the main purpose of the salt bath, or other media, is to conduct heat away from the walls of the reactor and control the reaction. Better operations are normally obtained when the reaction temperature employed is no greater than 20°–50° F. above the salt bath temperature. The temperature of the reactor, of course, will also depend to some extent upon the size of the reactor and the butane concentration.

The reaction may be conducted at atmospheric, superatmospheric, or below atmospheric pressure. The exit pressure will be at least slightly higher than the ambient pressure to ensure a positive flow from the reaction. The pressure of the inert gases must be sufficiently higher than the reaction temperature to overcome the pressure drop through the reactor.

Maleic anhydride may be recovered by a number of ways well-known to those skilled in the art. For example, the recovery may be by direct condensation or by absorption in suitable media, with specific operation and purification of the maleic anhydride. The following examples will serve to provide a fuller understanding of the invention, but it is to be understood that these examples are given for illustrative purposes only and will not be interpreted as limiting the invention in any way. In the examples the terms "conversion," "selectivity" and "yield" are defined as follows:

$$\text{Conversion \%} = \frac{\text{Moles n-butane reacted}}{\text{Moles n-butane in feed}} \times 100$$

$$\text{Selectivity \%} = \frac{\text{Moles maleic anhydride produced}}{\text{Moles n-butane feed consumed}} \times 100$$

$$\text{Yield Wt. \%} = (\text{Conversion}) \times (\text{Selectivity}) \times 169$$

EXAMPLE 1

Vanadium pentoxide, 91 g (0.5 mole), 1.5 l of 38 percent hydrochloric acid, and 4.4 g (0.03 mole) of molybdenum trioxide were added to a 3-l, 3-neck, round-bottom flask, equipped with a mechanical stirrer, reflux condenser, thermometer, and heated with an electric mantle. The solution at this time was red-brown in color. The solution was refluxed for ~2 hrs. at a temperature of 108° C., the color changing from red-brown to blue-green to blue during the reflux. At this time, 148 g (1.28 mole) of 85 percent $H_3PO_4$ were added to the solution, and distillation of $H_2O$—HCl was started using a side arm. A small amount of solids was observed in the reaction flask. The distillation was stopped, the contents filtered, and the distillation resumed. After 1200 ml of $H_2O$—HCl were removed, the distillation was terminated, leaving a viscous blue syrup in the flask.

Approximately one-half of this syrup was dissolved in 400 ml of methanol. This solution was placed in a 1-l, 1-neck, round-bottom flask, equipped with a reflux condenser, stirring bar, electric mantle, and placed on a hot plate stirrer. O-xylene, 150 ml, was added to the solution, which was then refluxed for 5.5 hrs. This solution was distilled until a viscous blue syrup, covered with a layer of o-xylene, was present. The o-xylene was decanted from the syrup, the syrup was placed in a plastic beaker and it was dried in a vacuum oven overnight, at 115°–120° C. and 18–20 in. Hg vacuum, with a small nitrogen purge passing through the oven. A small dark-brown crust which covered the blue catalyst was removed mechanically.

EXAMPLE 2

The catalyst prepared in Example 1 was crushed, combined with 5 percent by weight of graphite, and tabletted into cored 3/16" pellets having a 5 lb. crush strength. Analysis of this catalyst by X-ray diffraction gave 72 percent phase A and 16 percent VO(H$_2$PO$_4$)$_2$. A 6 cm$^3$ load of this catalyst (bulk density=0.9 g/cm$^3$) was placed in a minireactor under a 1.05 percent butane-synthetic air mixture and brought on stream as follows:

| | |
|---|---|
| 0–350° F. | 1.5 hrs. |
| 350° F. | 2 hrs. |
| 350–780° F. | 2 hrs. |
| 780° F. | Overnight |
| 830° F. | Next Day |

The space velocity of feed over this catalyst was 1200 hr$^{-1}$. The performance data for this catalyst are shown in Table I.

TABLE I

Performance Data for Catalyst in Example 2

| Days on Stream | Temperature (°F.) | Conversion (mole %) | Selectivity (mole %) | Yield (wt %) |
|---|---|---|---|---|
| 5 | 830 | 81 | 65 | 89 |
| 29 | 804 | 82 | 67 | 93 |
| 58 | 790 | 87 | 65 | 96 |
| 104 | 770 | 88 | 63 | 94 |
| 170 | 776 | 88 | 63 | 94 |

EXAMPLE 3

The remainder of the aqueous syrup from Example 1 was dried in a vacuum oven overnight, at 115°–120° C. and 18–20 in. Hg vacuum, with a small nitrogen purge passing through the oven. This blue-green catalyst was crushed, combined with 5 percent by weight of graphite, and tabletted into cored 3/16" pellets having a 5.5 lb. crush strength. The X-ray diffraction analysis of this catalyst gave 61 percent phase A and 16 percent VO(H$_2$PO$_4$)$_2$. A 6 cm$^3$ load of this catalyst was placed in a minireactor under a 1.05 percent n-butane in synthetic air mixture and brought on stream in a manner similar to Example 2. This catalyst, when evaluated at a feed space velocity of 1200 hr$^{-1}$, gave a best performance of 73 mole percent conversion, 63 mole percent selectivity, and 78 weight percent maleic anhydride yield after 49 days on stream at 831° F. This demonstrates the importance of treating the aqueous syrup with methanol or other suitable solvents.

EXAMPLE 4

Using the same experimental setup as described in Example 1, 91 g of vanadium pentoxide (0.5 mole), 1.5 l of 38 percent hydrochloric acid, and 4.4 g (0.03 mole) of molybdenum trioxide were refluxed for 2 hours and 20 minutes. The color changed from red-brown to blue during reflux, indicating a substantial amount of reduction of vanadium (V) to vanadium (IV). After the addition of 148 g of 85 percent ortho-phosphoric acid, the solution was filtered. Then 1150 ml of hydrochloric acid-water were removed by distillation, causing the temperature of the blue reaction solution to increase from 112° C. to 120° C. Isopropyl alcohol, 300 ml, and 75 ml of o-xylene were added to the blue syrup. The solution was refluxed for 1.5 hours, followed by distillation of solvent until the temperature of the mixture reached 110° C. The viscous syrup was poured into a teflon dish and dried in a vacuum oven overnight, at 120° C. and 18–20 in. of Hg vacuum, with a small nitrogen purge passing through the oven.

The dried catalyst was crushed, mixed with 5 percent graphite, and tabletted into cored 3/16" pellets having a 7–8 lb. crush strength. An X-ray diffraction analysis of this catalyst precursor gave 63 percent phase A and 13 percent vanadyl bisdihydrogenphosphate. A 6 cm$^3$ load of this catalyst was evaluated in a minireactor under a 1.05 percent n-butane in synthetic air mixture at a space velocity of 1200 hr$^{-1}$. After 29 days on stream, this catalyst gave 80 mole percent conversion, 63 mole percent selectivity, and 85 weight percent maleic anhydride yield at 832° F.

EXAMPLE 5

Using the previously described experimental setup, 91 g of vanadium pentoxide (0.5 mole), 1.5 l of 38 percent hydrochloric acid, and 8.58 g of uranium trioxide (0.03 mole) were refluxed at 112° C. for 4 hours. Again the color changed from red-brown to green to blue. After the addition of 148 g of 85 percent ortho-phosphoric acid (1.28 mole), hydrochloric acid-water was removed by distillation until the temperature of the blue syrup reached 123° C. After the syrup cooled to 70° C., one liter of methanol and 300 ml of o-xylene were added to the syrup and the mixture was refluxed for 2.5 hours at 70° C. Solvent was then removed by distillation until the temperature of the mixture reached 95° C. The syrup was poured into a teflon dish and dried in a vacuum oven overnight at 120°–125° C. and 2–3 in. of Hg vacuum, with a small nitrogen purge passing over the catalyst through the oven.

The dried catalyst precursor was crushed, mixed with 5 percent graphite, and tabletted into cored 3/16" pellets having a 5.9–7.0 lb. crush strength. X-ray diffraction analysis gave 73 percent phase A and 13 percent vanadyl bisdihydrogenphosphate. This catalyst (6 cm$^3$) was evaluated in a minireactor under 1.05 percent n-butane in synthetic air at a space velocity of 1200 hr$^{-1}$. Its performance after 98 days on stream was 79 mole percent conversion, 63 mole percent selectivity, and 84 weight percent yield of maleic anhydride at 829° F.

EXAMPLE 6

Using the same experimental setup, 91 g of vanadium pentoxide (0.5 mole), 1.5 l of 38 percent hydrochloric acid, and 4.4 g of molybdenum trioxide (0.03 mole) were refluxed at 112° C. for 2½ hours. At this time, 148 g of 85 percent ortho-phosphoric acid (1.28 mole) were added to the reaction solution. Hydrochloric acid-water (about 1225 ml) was removed until the reaction solution reached 128.5° C. When the solution cooled to 75° C., 1 l of methanol and 300 ml of o-xylene were added, and the solution was refluxed for 24 hours. After 18 hours of reflux, light blue precipitate was observed in the solution. Approximately 500 ml of solvent were removed by distillation. The contents of the flask were poured into a 1-l beaker and were dried in a vacuum oven overnight, at 120°–130° C. and 1–15 in. of Hg vacuum, with a small nitrogen purge passing through the oven.

The dry catalyst precursor was crushed, mixed with 5 percent graphite, and formed into cored 3/16" pellets having a 6–6.5 lb. crush strength. The X-ray diffraction analysis of the catalyst precursor gave 81 percent phase A and no vanadyl bisdihydrogenphosphate.

The catalyst (6 cm$^3$) was evaluated in a minireactor under 1.05 percent n-butane in synthetic air at a space velocity of 1200 hr$^{-1}$. Its performance is summarized in Table II.

TABLE II

| | Performance of Catalyst in Example 6 | | | |
|---|---|---|---|---|
| Days on Stream | Temperature (°F.) | Conversion (mole %) | Selectivity (mole %) | Yield (wt %) |
| 5 | 780 | 62 | 67 | 70 |
| 11 | 802 | 85 | 65 | 93 |
| 39 | 814 | 86 | 66 | 95 |
| 52 | 792 | 88 | 63 | 93 |

EXAMPLE 7

Using the previously-described experimental setup, 91 g of vanadium peroxide (0.5 mole), 1.5 l of 38 percent hydrochloric acid, and 4.4 g of molybdenum trioxide (0.03 mole) were refluxed for 3 hours at 112° C. Following this reflux, 138 g of 85 percent ortho-phosphoric acid (1.2 mole) were added to the blue solution and solvent was removed by distillation until the temperature of the solution reached 127° C. When the viscous solution cooled to 80° C., 250 ml of methanol were added and the solution was allowed to reflux for 15 hours at 75° C. After distilling off about 100 ml of solvent, the contents of the flask were poured into a teflon dish and placed in a vacuum oven overnight, at 120°-130° C. and 10 in. of Hg vacuum, with a small nitrogen purge passing through the oven.

The dried catalyst precursor was crushed, mixed with 5 percent graphite, and formed into cored 3/16" pellets having a 3 lb. crush strength. The X-ray diffraction analysis of this catalyst precursor gave 85 percent phase A and no vanadyl bisdihydrogenphosphate. The catalyst (6 cm$^3$) was evaluated in a minireactor under 1.05 percent n-butane in synthetic air at a space velocity of 1200 hr$^{-1}$. Its performance is documented in Table III. The excellent performance of this catalyst demonstrates that different catalyst P/V ratios are effective and that good catalysts can be prepared without using o-xylene, although the use of o-xylene is preferred for consistency in catalyst performance between repeat preparations.

TABLE III

| | Performance of Catalyst in Example 7 | | | |
|---|---|---|---|---|
| Days on Stream | Temperature (°F.) | Conversion (mole %) | Selectivity (mole %) | Yield (wt %) |
| 6 | 783 | 77 | 68 | 88 |
| 15 | 784 | 86 | 67 | 97 |
| 41 | 783 | 87 | 67 | 99 |
| 78 | 770 | 89 | 65 | 98 |

EXAMPLE 8

Using the standard setup described earlier, 91 g of vanadium pentoxide (0.05 mole), 1.5 l of 38 percent hydrochloric acid, and 4.4 g of molybdenum trioxide (0.03 mole) were refluxed for 3 hours at 112° C. At this time, 148 g of 85 percent ortho-phosphoric acid (1.28 mole) were added to the blue solution. Solvent was distilled until the temperature of the reaction solution reached 130° C. When the blue syrup cooled to 75° C., 250 ml of tetrahydrofuran were added to the syrup, and the solution was refluxed for 17 hours. After about 14 hours, some precipitate was noticed in the solution. After distilling off 100-200 ml of liquid, the contents of the flask were poured into a teflon dish and placed in a vacuum oven overnight, at 120°-130° C. and 10 in. of Hg vacuum, with a small nitrogen purge passing through the oven.

The dried catalyst precursor was crushed, mixed with 5 percent graphite, and formed into 3/16" cored pellets having a 5.5-6 lb. crush strength. Analysis of the precursor by X-ray diffraction showed 77 percent phase A and 2 percent vanadyl bisdihydrogenphosphate. The catalyst (6 cm$^3$) was evaluated in a minireactor under 1.05 percent n-butane in synthetic air at a space velocity of 1200 hr$^{-1}$. After 25 days on stream, the catalyst performance was 81 mole percent conversion, 64 mole percent selectivity, and 88 weight percent yield of maleic anhydride. This example shows that solvents other than alcohols can be used to prepare good-performing catalysts using this procedure, although methanol is preferred.

EXAMPLE 9

Using the standard reaction setup, 91 g of vanadium pentoxide (0.5 mole) and 0.5 l of 38 percent hydrochloric acid were refluxed for 10 minutes at 111° C. After the reaction solution was cooled to 80° C., 11.77 g of zinc metal (0.18 mole) were added slowly to the reaction solution. The solution was allowed to reflux for 1 hour before 138 g of 85 percent ortho-phosphoric acid (1.2 mole) were added. About 440 ml of solvent were distilled until the solution temperature reached 130° C. After the solution temperature decreased to 70° C., 400 ml of methanol and 100 ml of o-xylene were added to the dark-blue solution and it was allowed to reflux for 20 hours. Solvent (295 ml) was removed by distillation and the syrup was poured into a teflon dish. The syrup was dried in a vacuum oven overnight, at 140° C. and 10 in. of Hg vacuum, with a small nitrogen purge passing through the oven.

The dried catalyst precursor was crushed, mixed with 5 percent Sterotex, and formed into 3/16" cored pellets having a 8-10 lb. crush strength. The catalyst (6 cm$^3$) was evaluated in a minireactor under a 1.05 percent n-butane in synthetic air mixture at a space velocity of 1200 hr$^{-1}$. After 56 days on stream, the catalyst gave a performance of 77 mole percent conversion, 63 mole percent selectivity, and 82 weight percent maleic anhydride yield at 828° F.

EXAMPLE 10

Using the standard experimental setup, 91 g of vanadium pentoxide, 1.5 l of 38 percent hydrochloric acid, and 6.96 g of tungsten trioxide (0.03 mole) were refluxed for 2.5 hours at 112° C. Following the addition of 138 g of 85 percent ortho-phosphoric acid (1.2 mole), solvent was removed by distillation until the temperature of the reaction solution reached 130° C. When the solution cooled to 70° C., 500 ml of methanol were added and the solution refluxed for 16 hours. Solvent (200-300 ml) was removed by distillation, and the blue syrup was poured into a teflon dish. The material was dried in a vacuum oven overnight, at 120°-130° C. and 10 in. of Hg vacuum, with a small purge of nitrogen passing through the oven.

The dried catalyst precursor was crushed, mixed with 5 percent Sterotex, and formed into 3/16" cored pellets having a 7-8.5 lb. crush strength. The catalyst (6 cm³) was evaluated in a minireactor under 1.05 percent n-butane in synthetic air at a space velocity of 1200 hr⁻¹. After 56 days on stream, the performance of the catalyst was 82 mole percent conversion, 61 mole percent selectivity, and 84 weight percent yield of maleic anhydride at 817° F.

EXAMPLE 11

91 g of vanadium pentoxide, 4.4 g of molybdenum trioxide, and 1.5 l of 38 percent hydrochloric acid were charged to a 3-l, 3-neck, round-bottom flask equipped with a mechanical stirrer, reflux condenser, and thermocouple, and heated with an electric mantle. The red-brown slurry was allowed to reflux for 3 hours. During this reflux, the vanadium pentoxide dissolved and the color turned to blue. At this time, 148 g of 85 percent ortho-phosphoric acid were added to the solution, and distillation of the water-hydrochloric acid solvent was started. Solvent was removed until the temperature of the blue syrup reached 130° C. Methanol (250 ml) was added to the aqueous syrup, and the solution refluxed for about 17 hours. The contents of the flask were dried in a vacuum oven overnight, at 120°–130° C. and 7 in. of Hg vacuum, with an air purge passing through the oven.

The dried catalyst precursor was crushed, mixed with 5 percent graphite, and formed into 3/16" cylinders having a 3-3.5 lb. crush strength. A 6 cm³ volume of this catalyst (6.02 g) was loaded into a minireactor and evaluated with a feed of 1.1 percent n-butane in synthetic air at a space velocity of 1200 hr⁻¹. After 21 days on stream, this catalyst gave a maximum yield of 85 weight percent maleic anhydride at 793° F. The conversion was 81 mole percent, and the selectivity 62 mole percent.

EXAMPLE 12

Using the same experimental setup as described in Example 11, 91 g of vanadium pentoxide, 4.4 g of molybdenum trioxide, and 1.5 l of 38 percent hydrochloric acid were charged to the 3-l flask. After 3 hours of reflux, 148 g of 85 percent ortho-phosphoric acid were added, and solvent was distilled until the temperature of the blue syrup reached 133° C. Methanol (250 ml) and 10 g of phthalic anhydride were added to the aqueous syrup. After the solution refluxed for about 26 hours, a heavy light blue precipitate was present in the flask. The contents of the flask were dried in a vacuum oven overnight, at 130° C. and 10 in. of Hg vacuum, with an air purge passing through the oven.

The dried catalyst precursor was crushed, mixed with 5 percent graphite, and formed into 3/16" cylinders having a 2.5-3 lb. crush strength. A 6 cm³ volume of this catalyst (5.7 g was loaded into a minireactor and evaluated with a feed of 1.1 percent n-butane in synthetic air at a space velocity of 1200 hr⁻¹. This catalyst gave a 91 weight percent yield of maleic anhydride with a conversion of 81 mole percent and selectivity of 67 mole percent at 825° F. after 21 days on stream. A maximum yield of 98 weight percent of maleic anhydride was obtained at 802° F. after 60 days on stream.

This example shows that the addition of 10 g of phthalic anhydride significantly improved the yield of this catalyst over the catalyst in Example 11 which was prepared without phthalic anhydride.

EXAMPLE 13

A large quantity of aqueous catalyst syrup was prepared by charging a 12-l flask with 10 l of 38 percent hydrochloric acid, 637 g of vanadium pentoxide, and 30.8 g of molybdenum trioxide. After a 4-hour reflux, 1036 g of 85 percent ortho-phosphoric acid were added to the blue solution. Solvent was removed by distillation until the syrup temperature reached 131° C. Methanol (1160 ml) was added to the syrup to give 2 l of blue methanolic catalyst solution.

EXAMPLES 14–21

The catalysts in Examples 14–21 were prepared using the methanolic catalyst solution described in Example 13. 500 ml of methanol and one of the compounds shown in Table IV were added to 200 ml of this catalyst solution. The solutions were refluxed overnight resulting in the precipitation of blue material. The flask contents were dried in a vacuum oven overnight, at 120° C. and 0-3 in. of Hg vacuum, with an air purge passing through the oven.

The dried precursors were crushed, mixed with 5 percent graphite, and formed into 3/16" cylinders having 6-9 lb. crush strengths. These catalysts were evaluated as described in previous examples giving the results shown in Table IV. The catalysts in Examples 15-21, prepared in the presence of aromatic acids and anhydrides, all gave increased yields and were more active, as indicated by the lower temperatures than Example 14 and Example 11, demonstrating the usefulness of these compounds in catalyst preparation. Especially noteworthy is the catalyst in Example 16 which gave a consistent 98-100 weight percent maleic anhydride yield for 70 days at 753°–802° F.

TABLE IV

Performance of Catalysts in Examples 14–21

| Example | Additive | Days on Stream | Temp. (°F.) | Conv. mole (%) | Selec. mole (%) | Yield (wt %) |
|---|---|---|---|---|---|---|
| 14 | 200 ml o-xylene | 30 | 827 | 81 | 65 | 88 |
| 15 | 10 g phthalic anhydride | 29 | 821 | 84 | 63 | 89 |
| 16 | 30 g phthalic anhydride | 30 | 810 | 86 | 66 | 95 |
| 17 | 10 g phthalic acid | 30 | 806 | 86 | 64 | 94 |
| 18 | 10 g trimesic acid | 30 | 825 | 83 | 64 | 89 |
| 19 | 8.6 g hemimellitic acid | 29 | 804 | 81 | 66 | 90 |
| 20 | 10 g pyromellitic acid | 28 | 791 | 80 | 66 | 89 |
| 21 | 10 g trimellitic anhydride | 30 | 795 | 85 | 67 | 95 |

EXAMPLE 22

Another large quantity of aqueous catalyst syrup was prepared in a 12-l flask using 546 g of vanadium pentoxide, 26.4 g of molybdenum trioxide, and 9 l of 38% hydrochloric acid. After a 4-hour reflux, 888 g of 85 percent ortho-phosphoric acid were added to the blue solution. Solvent was removed by distillation until the syrup temperature reached 131° C. Methanol (1300 ml) was added to the syrup to give 2 l of blue methanolic catalyst solution.

EXAMPLES 23-27

The catalysts in Examples 23-27 were prepared using the methanolic catalyst solution described in Example 22. 500 ml of methanol and one of the compounds shown in Table V were added to 325 ml of this catalyst solution. The solutions were refluxed overnight resulting in the formation of blue precipitate. The flask contents were dried in a vacuum oven overnight, at 130°-135° C. and 0-3 in. of Hg vacuum, with an air purge passing through the oven.

The dried catalyst precursors were crushed, mixed with 5 weight percent graphite, and formed into 3/16" cylinders having 3-8 lb. crush strengths. These catalysts were evaluated as described previously, giving the results shown in Table V. The catalysts having aromatic acid or aromatic anhydride additives gave better yields than the catalyst in Example 23 which had no additive.

TABLE V
Performance of Catalysts in Examples 23-27

| Example | Additive | Days on Stream | Temp. (°F.) | Conv. mole (%) | Selec. mole (%) | Yield (wt %) |
|---|---|---|---|---|---|---|
| 23 | None | 26 | 819 | 81 | 60 | 82 |
| 24 | 0.3 mole phthalic anhydride | 27 | 817 | 83 | 63 | 88 |
| 25 | 0.3 mole trimellitic anhydride | 28 | 812 | 85 | 60 | 87 |
| 26 | 0.3 mole benzoic acid | 28 | 818 | 84 | 65 | 92 |
| 27 | 0.3 mole toluic acid | 28 | 829 | 81 | 65 | 89 |

We claim:

1. A process for the manufacture of a phosphorus-vanadium catalyst suitable for use in the manufacture of maleic anhydride, which process comprises reacting in an aqueous medium a vanadium compound and inorganic acid, then adding ortho-phosphoric acid to form a soluble vanadium-phosphorus catalyst, removing the acidified water, and adding an aliphatic alcohol having about 1 to about 8 carbon atoms, and either an aromatic acid, or an aromatic anhydride, or a mixture of these, removing the alcohol, and removing the aromatic acid and aromatic anhydride, and drying the catalyst syrup under vacuum of about 0 to about 300 mm Hg at a temperature of about 90° to about 150° C. to produce the solid catalyst.

2. The process of claim 1 wherein the vanadium compound is vanadium pentoxide.

3. The process of claim 2 wherein the alcohol is methanol and the inorganic acid is HCl, and the orthophosphoric acid is 85 to 95 percent ortho-phosphoric acid.

4. The process of claim 2 wherein the anhydride added is phthalic anhydride.

5. The process of claim 2 wherein the anhydride added is trimellitic anhydride.

6. The process of claim 2 wherein the acid added is phthalic acid.

7. The process of claim 2 wherein the acid added is trimesic acid.

8. The process of claim 2 wherein the acid added is hemimellitic acid.

9. The process of claim 2 wherein the acid added is pyromellitic acid.

10. The process of claim 2 wherein the acid added is benzoic acid.

11. The process of claim 2 wherein the acid added is toluic acid.

12. A process for the manufacture of a phosphorus-vanadium-metal oxide catalyst suitable for use in the manufacture of maleic anhydride, which process comprises reacting in an aqueous medium a vanadium compound and inorganic acid and metal oxide, then adding ortho-phosphoric acid to form a soluble vanadium-phosphorus-metal oxide catalyst, removing the acidified water, and adding an aliphatic alcohol having about 1 to about 8 carbon atoms, and either an aromatic acid, or an aromatic anhydride, or a mixture of these, removing the alcohol, and removing the aromatic acid and aromatic anhydride, and drying the catalyst syrup under vacuum of about 0 to about 300 mm Hg at a temperature of about 90° to about 150° C. to produce the solid catalyst.

13. The process of claim 12 wherein the vanadium compound is vanadium pentoxide.

14. The process of claim 13 wherein the alcohol is methanol and the inorganic acid is HCl, and the ortho-phosphoric acid is 85 to 95 percent ortho-phosphoric acid.

15. The process of claim 13 wherein the anhydride added is phthalic anhydride.

16. The process of claim 13 wherein the anhydride added is trimellitic anhydride.

17. The process of claim 13 wherein the acid added is phthalic acid.

18. The process of claim 13 wherein the acid added is trimesic acid.

19. The process of claim 13 wherein the acid added is hemimellitic acid.

20. The process of claim 13 wherein the acid added is pyromellitic acid.

21. The process of claim 12 wherein the acid added is benzoic acid.

22. The process of claim 12 wherein the acid added is toluic acid.

23. A process for the manufacture of a phosphorus-vanadium-metal oxide catalyst, suitable for use in the manufacture of maleic anhydride, which process comprises reacting in an aqueous medium vanadium compound and inorganic acid and molybdenum oxide, then adding ortho-phosphoric acid to form a soluble vanadium-phosphorus-molybdenum oxide catalyst, removing the acidified water and adding an aliphatic alcohol having about 1 to about 8 carbon atoms, and either an aromatic acid, or an aromatic anhydride, or a mixture of these, removing the alcohol, and removing the aromatic acid and aromatic anhydride, and drying the catalyst syrup under vacuum of about 0 to about 300 mm Hg at a temperature of about 90° to about 120° C. to produce the solid vanadium-phosphorus-molybdenum oxide catalyst.

24. The process of claim 23 wherein the vanadium compound is vanadium pentoxide.

25. The process of claim 23 wherein the alcohol is methanol.

26. The process of claim 23 wherein the anhydride added is phthalic anhydride.

27. The process of claim 23 wherein the anhydride added is trimellitic anhydride.

28. The process of claim 23 wherein the acid added is phthalic acid.

29. The process of claim 23 wherein the acid added is trimesic acid.

30. The process of claim 23 wherein the acid added is hemimellitic acid.

31. The process of claim 23 wherein the acid added is pyromellitic acid.

32. The process of claim 23 wherein the acid added is benzoic acid.

33. The process of claim 23 wherein the acid added is toluic acid.

34. The process of claim 23 wherein the inorganic acid is HCl.

35. The process of claim 24 wherein the ortho-phosphoric cid is 85 to 95 percent ortho-phosphoric acid.

* * * * *

UNITED STATES PATENT OFFICE
CERTIFICATE OF CORRECTION

Patent No. 4,510,259            Dated April 9, 1985

Inventor(s) CARL A. UDOVICH  -  ROBERT C. EDWARDS

It is certified that error appears in the above-identified patent and that said Letters Patent are hereby corrected as shown below:

Patent

| Column | Line | |
|---|---|---|
| 1 | 8 | After "1982"  Add -- , now -- |
| 1 | 26 | "trand" should read -- trend -- |
| 3 | 25 | "the" (1st occurrence) should read --The -- |
| 7 | 20 | "peroxide" should read -- pentoxide -- |
| 7 | 61 | "0.05" should read -- 0.5 -- |
| 9 | 57 | After "(5.7g  Add -- ) -- |

Signed and Sealed this

Fifteenth Day of October 1985

[SEAL]

Attest:

Attesting Officer

DONALD J. QUIGG

Commissioner of Patents and Trademarks—Designate